(12) United States Patent
Johnson et al.

(10) Patent No.: US 8,439,027 B2
(45) Date of Patent: May 14, 2013

(54) DOOR CONTROL MECHANISM

(75) Inventors: Lawrence Byron Johnson, Bellingham, WA (US); Tadeusz Karabin, Bellingham, WA (US)

(73) Assignee: Wood Stone Corporation, Bellingham, WA (US)

( * ) Notice: Subject to any disclaimer, the term of this patent is extended or adjusted under 35 U.S.C. 154(b) by 1694 days.

(21) Appl. No.: 11/766,039

(22) Filed: Jun. 20, 2007

(65) Prior Publication Data

US 2008/0149086 A1     Jun. 26, 2008

Related U.S. Application Data

(60) Provisional application No. 60/871,252, filed on Dec. 21, 2006.

(51) Int. Cl.
    *F23M 7/00*          (2006.01)

(52) U.S. Cl.
    USPC ........... 126/191; 126/192; 126/194; 126/197; 126/19 R; 126/273 R; 267/172

(58) Field of Classification Search .................. 126/190, 126/191, 192, 194, 197, 19 R, 273 R, 39 A, 126/39 B, 39 BA, 39 E, 39 H, 39 N; 267/170, 267/172, 173, 179; 16/49, 53, 60, 63, 64, 16/65, 50, 71, 78, 79, 80
See application file for complete search history.

(56) References Cited

U.S. PATENT DOCUMENTS

| 539,741 | A | | 5/1895 | Ingram | |
|---|---|---|---|---|---|
| 1,206,817 | A | | 12/1916 | Cuthbert | |
| 2,320,772 | A | | 6/1943 | Doman | |
| 3,344,462 | A | | 10/1967 | Webster | |
| 3,955,865 | A | * | 5/1976 | Wilson | 126/191 |
| 4,084,572 | A | * | 4/1978 | Schettl et al. | 126/200 |
| 4,368,721 | A | * | 1/1983 | Kroupa | 126/4 |
| 4,787,121 | A | | 11/1988 | Racenis et al. | |
| 4,817,240 | A | * | 4/1989 | Sovis et al. | 16/297 |
| 5,060,344 | A | | 10/1991 | Cress | |
| 5,208,945 | A | * | 5/1993 | Dodd | 16/358 |
| 5,220,747 | A | * | 6/1993 | Cherry et al. | 49/386 |
| 5,241,947 | A | * | 9/1993 | Sandolo | 126/21 A |
| 5,485,816 | A | * | 1/1996 | Cox et al. | 126/25 R |
| 5,522,656 | A | * | 6/1996 | Jenkins | 292/79 |
| 6,557,959 | B1 | | 5/2003 | King | |

* cited by examiner

*Primary Examiner* — John K Fristoe, Jr.
*Assistant Examiner* — Jessica Cahill
(74) *Attorney, Agent, or Firm* — Dwayne E. Rogge; Schacht Law Office, Inc.

(57) ABSTRACT

A door control mechanism which is attached near the hinge region of a door to bias the door to a closed orientation, and after a prescribed location, bias the door toward an open location to a sufficient degree such that the door is noticeably open. The door control mechanism in one form may have a cam extension that engages a spring member to supply stored energy to and from the spring member to bias the door closed and to bias the door open after a prescribed amount of rotation.

13 Claims, 17 Drawing Sheets

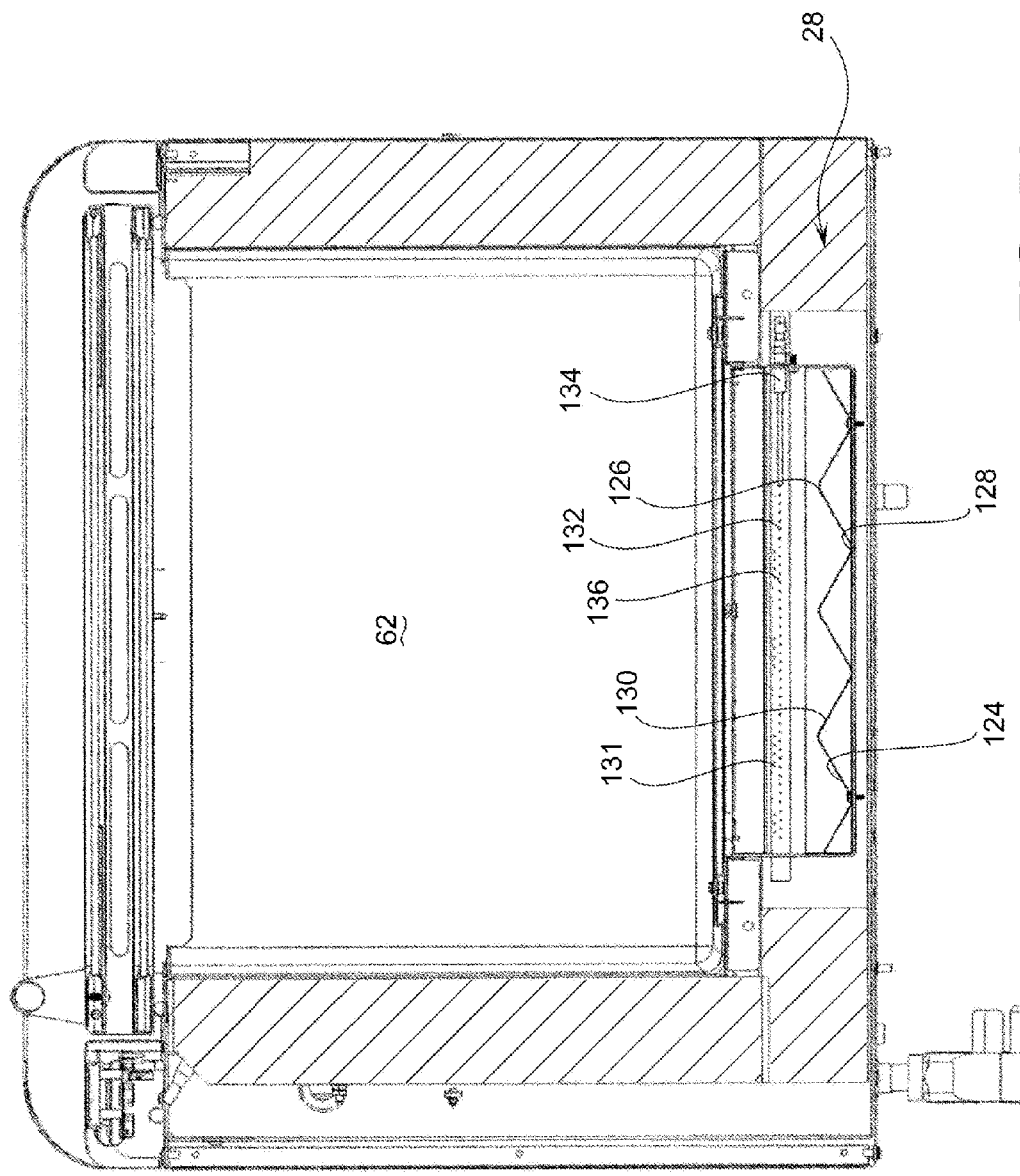

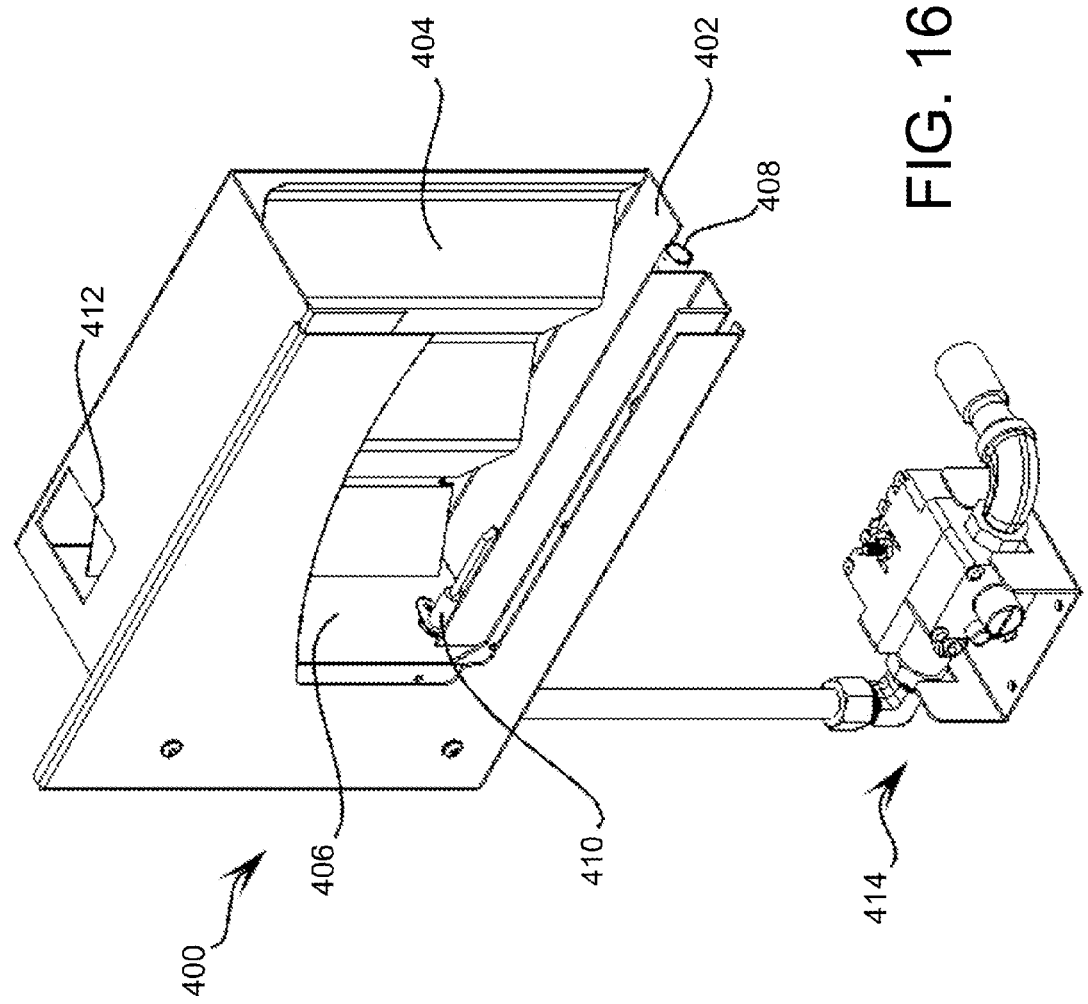

DOOR CONTROL MECHANISM

RELATED APPLICATIONS

This application claims priority benefit of U.S. Ser. No. 60/871,252, filed Dec. 21, 2006 and U.S. Ser. No. 11/747,732 filed May 11, 2007.

BACKGROUND OF THE DISCLOSURE

Oftentimes, it is desirable to have a door control system on an apparatus such as an oven which locks the door or at least biases the door to a closed orientation. Other types of devices have been attempted, such as latches and magnets. Latches and other types of connectors have the inherent problem of sanitation in that they are difficult to keep clean in a cooking environment where the door control mechanism is attached to an oven. Items like magnets can be effective to supply a closing force; however, many natural magnets are temperature sensitive and the magnetic properties can break down after a certain temperature threshold.

Another issue with doors in certain environments, such as culinary environments, is that it is desirable to know whether a door (such as an oven door) is closed or open. Having a door partially closed can be problematic because heat may be lost, or a switch mechanism may turn off the heating element if the door is not sufficiently visibly open and the chef or other person attending to the door does not notice the door is not entirely closed.

Therefore, there is a need for a door which biases to a closed position, and after the prescribed amount of rotation, biases to an open orientation. Further, as shown herein in one embodiment, the force placed on the door to open or close the door does not occur through the entire range of motion, but in one preferred form, after the door is open beyond say 20°, there is not an opening or closing force acting thereon. Rather, in one form there can be a frictional force to ensure the door is maintained at a certain orientation without rotating open or closed, which is an issue if the oven is not properly leveled (or more specifically, the axis of rotation of the door is not in line with the flux field of gravity).

SUMMARY OF THE DISCLOSURE

Described in detail herein is a door control mechanism configured to attach to a door, the door control mechanism has a base plate which in one form is a separate member or can be integrated within an overall assembly such as a floor region of a door. A rotary member attached to the door and having a cam extension. There is also a base unit and a spring member. The spring member is positioned to engage the cam extension at a cam engagement portion at an orientation when the rotary member is in a closed orientation with respect to the base unit. The cam extension is configured to reposition the spring member to a higher stored energy orientation when the door attached to the rotary member is in a partially closed orientation and the spring member is configured to release some stored energy to bias the door fully closed.

The door control mechanism in one form has the rotary member having a surface defining an arcuate path where a travel limiting pin is attached to the base plate and configured to travel along the arcuate path to limit the range of motion of the rotary member. In another form the surface defining the arcuate path has an open stop surface and a closed stop surface. A door opened spring stop in one form can be attached to the rotary member and configured to engage a stop surface attached to the base plate where the door opened spring stop engages the stop surface when the door is in an extreme open orientation.

The door opened spring stop can be a cantilevered spring member and a door closed sensor is operatively configured to detect when the rotary remember is in a closed orientation. In one form the spring member is a cantilevered spring and the spring member has a secondary spring element that is positioned at an opposing region of a cantilevered portion of the spring member. In this embodiment the secondary spring element is adjustable to provide various spring force and position of the cam engagement portion into closer engagement toward the rotary member.

In one application a door control mechanism for an oven door that is pivotally attached to an oven having an interior cooking chamber. Another way of defining the door control mechanism is to provide a rotational member, having an attachment point that is configured to attach to the door of the rotary member having a cam surface and having a forward and rearward sloping portion. There is further a base unit having a cam engagement portion, the cam engagement portion configured to engage the cam extension of the rotary member when the rotary member is in a closed orientation and the door is closed with respect to the oven where the cam engagement member is engaging the rearward surface of the rotary member. When the door is repositioned toward an open orientation, the cam engagement portion transfers from engaging the rearward surface past a high center point to a forward surface to bias the door toward the open orientation. The cam engagement member can be a spring member which repositions as the door moves from a closed orientation to an open orientation and vice versa. In one form the cam member is a spring member to reposition when engaging the cam engagement member when repositioning from a closed orientation to an open orientation and vice versa. On preferred method of having the cam member is where the cam engagement surface is a bearing member configured to rotate.

The detailed description discloses a more specific teaching of carrying out one such apparatus.

BRIEF DESCRIPTION OF THE DRAWINGS

FIG. 5A shows a top sectional view of the oven showing a top view of the flame chamber;

FIG. 16 shows a concept of a discrete flame chamber shown in an isometric sectional view.

DESCRIPTION OF THE PREFERRED EMBODIMENTS

Figure 1:
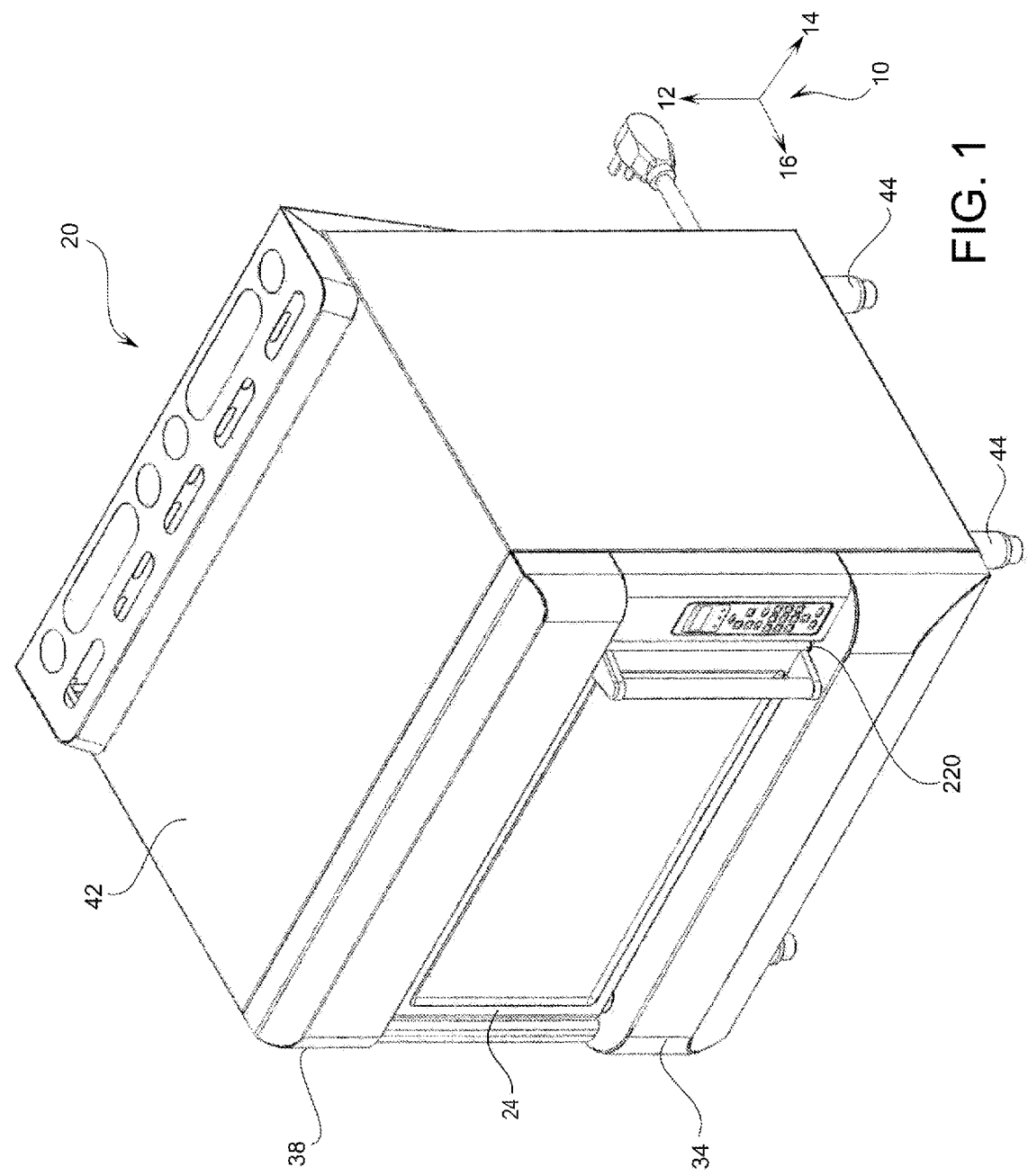
FIG. 1 shows an isometric view of the flame chambered oven.

As shown in FIG. 1, there is a flame oven 20 which is shown in one form as a tabletop design, but of course can take a variety of installation methods. Before beginning the detailed description of one embodiment of the flame oven, there will first be a description of an axis system 10 as shown FIG. 1. The axis 12 indicates a vertical direction and the axis 14 indicates a lateral direction, where for general purposes of the description, the arrow 14 will be referred to as the right, and the opposing direction will be herein referred to as the left. The axis substantially orthogonal to the vertical and lateral directions is defined as a transverse axis, and for purposes of general description, the arrow 16 points forward and the opposing direction will be referred to as rearward. The axis system 10 is intended for general description purposes and is not intended to limit the concept in scope, and is provided to aid in the general orientation of the components. Further, the axes indicate a general direction, and are not necessarily perfectly orthogonal to one another.

Figure 2:
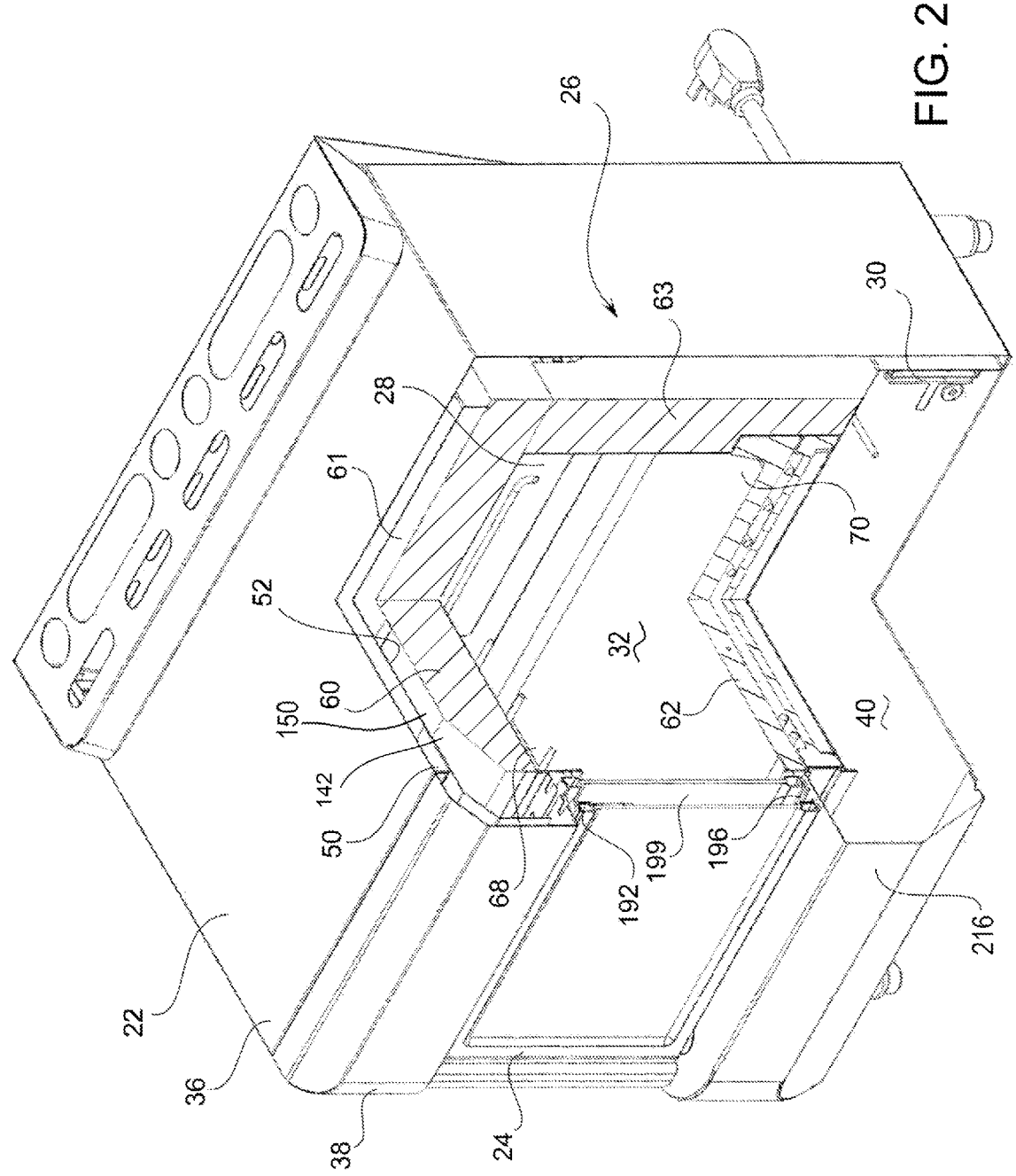
FIG. 2 shows a partial sectional view of the flame chambered oven showing the central cooking chamber and the chamber heater as well as the base plate heating assembly.

Referring still to FIG. 1, the outer structure of the flame oven 20 is generally shown. FIG. 2 shows a partial sectional view where the general components of the oven can be more readily identified. The flame oven is comprised of a housing 22, a door 24, a first heating system 26, and a flame chamber assembly 28. As further shown in FIG. 2, the flame oven in a preferred form has an electronic section 30 and various components define a cooking chamber 32.

Figure 3:
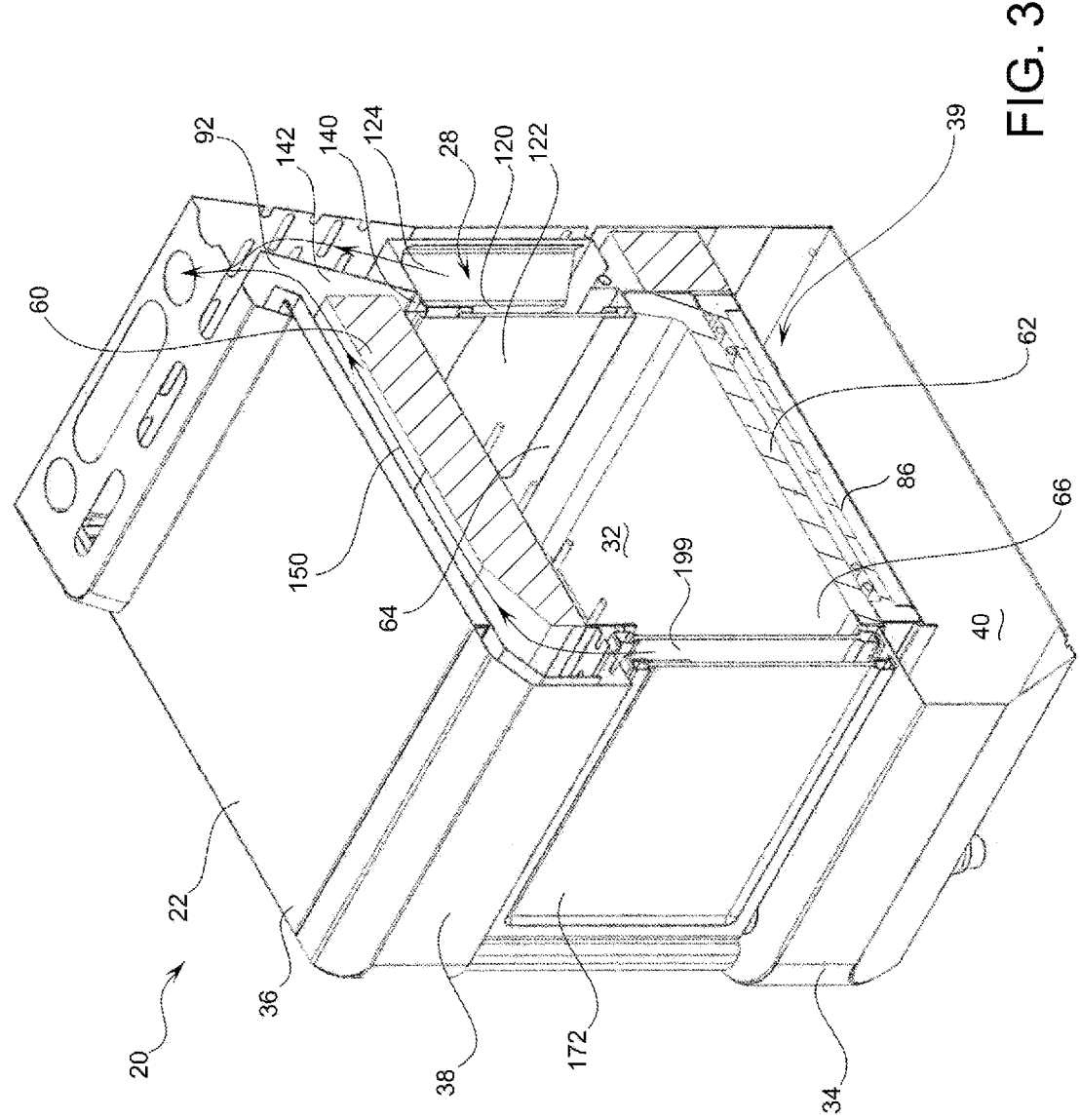
FIG. 3 shows a sectional view of the oven showing the cooking chamber as well as the flame chamber positioned in a transverse rearward orientation with respect to the cooking chamber.

Referring now to FIG. 3, there will first be a description of the housing 22 where the flame oven 20 can be seen in a sectional isometric view. In general, the housing comprises a base portion 34 and an upper portion 36. The front regions of the upper portion 36 of the base portion 34 comprise the front panel 38. As shown in FIG. 3, the base portion of the housing 22 defines a lower chamber 40. The lower chamber 40 is, in part, insulated by the insulation layer lower plate 86 of the base heating assembly 39. As described further herein, the lower chamber generally provides cooler air to be passed vertically through the door chamber 199 and up through the upper convection vent/flame exhaust 142, where such current is drawn from the rising hot combusted gas of the flame chamber assembly described further herein.

The housing as shown in FIG. 1 further comprises an outer casing 42 which in one form can be a stainless steel. Positioned at the lower portion of the base portion are a plurality of support legs 44 which can be utilized to support the unit in one form. Of course, the flame oven 20 could be mounted in a variety of ways.

Now referring to FIG. 2, the upper portion 36 of the housing 22 comprises, in one form, an inner shell which in part defines the upper ventilation chamber 50. The inner shell further has the lower surface 52, which in part defines the upper convection vent 142 described further herein.

Figure 4:
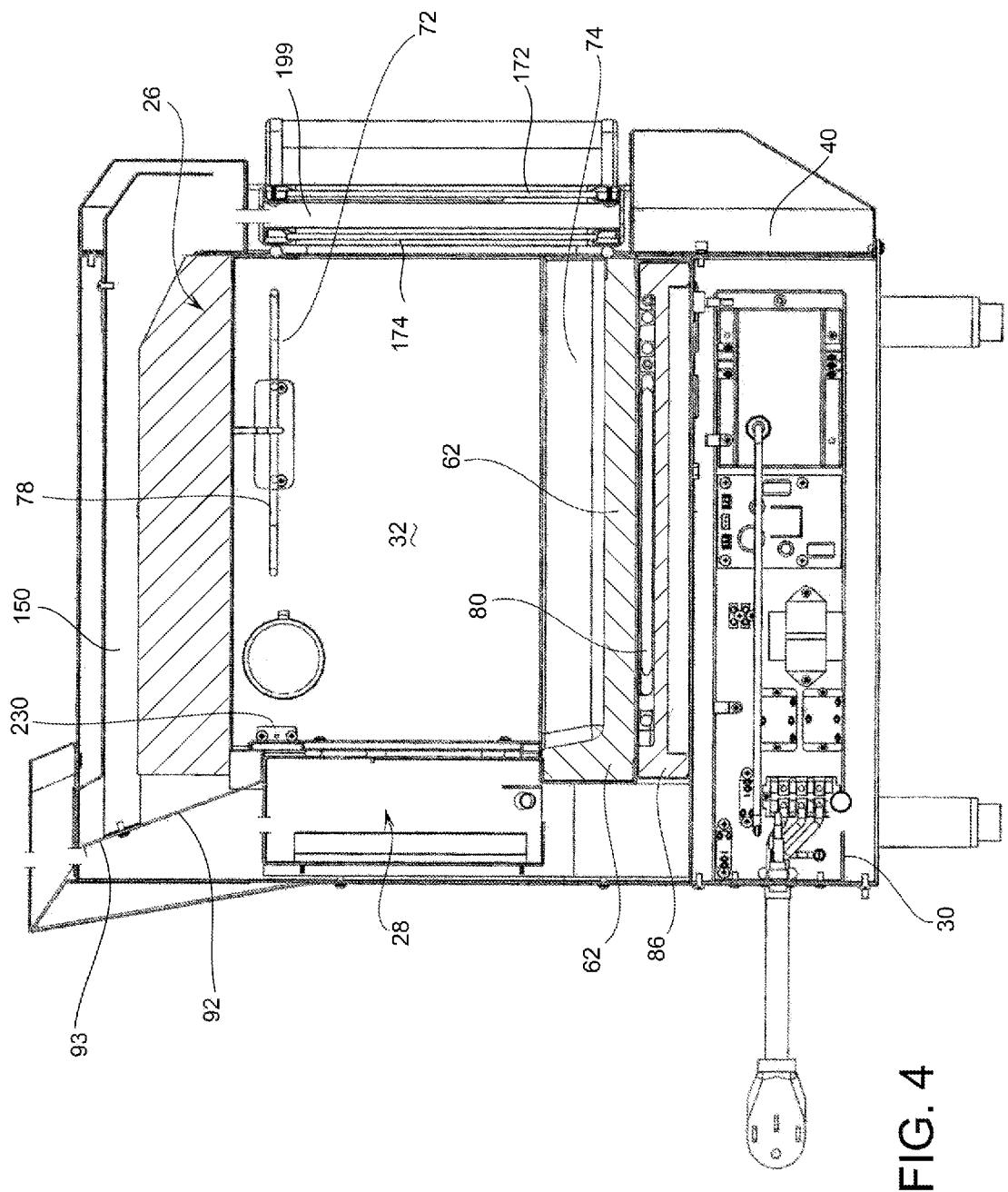
FIG. 4 shows a side profile sectional view showing the power electronics as well as the central cooking chamber.

The cooking chamber 32 as shown in FIG. 3 is contained within the housing 22 and is operatively configured to cook food items therein. The cooking chamber is defined, at least in part, by the upper heat containment member 60 having the upper surface and the base plate 62. As shown in FIG. 2, positioned at the right lateral region of the flame oven 20 is a lateral heat containment member 63 where a similar type member is positioned at the opposing lateral region of the flame oven 20. The cooking chamber 32 has longitudinally rearward and forward portions 64 and 66 as shown in FIG. 3, as well as first and second lateral portions 68 and 70 such as that shown in FIG. 2. As shown in FIG. 4, the cooking chamber further comprises an upper region 72 and a lower region 74. As best shown in FIG. 3, positioned in the longitudinally rearward portion 64 of the cooking chamber 62 is the flame chamber assembly 28 which is described in detail further herein, but comprises in part the transparent member 122 which at least partially isolates the flame within the flame chamber 120 from the cooking chamber. The transparent member 122 of the flame chamber could be double-sided glass or thermal insulated transparent member which does not provide heat to the cooking chamber. In another form a piece of glass which provides a greater amount of heat transfer from the flame chamber can be employed.

Figure 9:
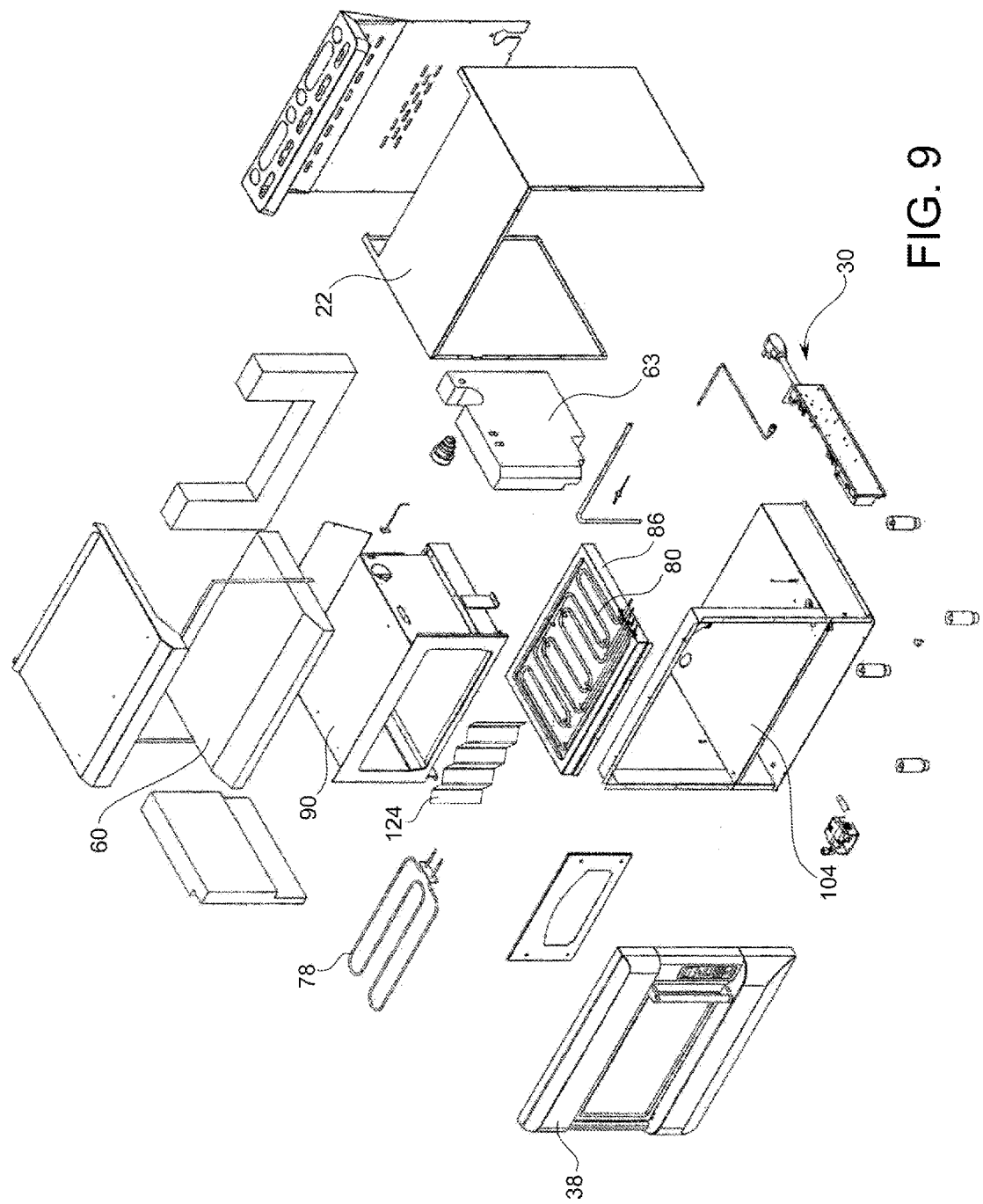
FIG. 9 shows a general exploded view of the oven in one form.
Figure 10:
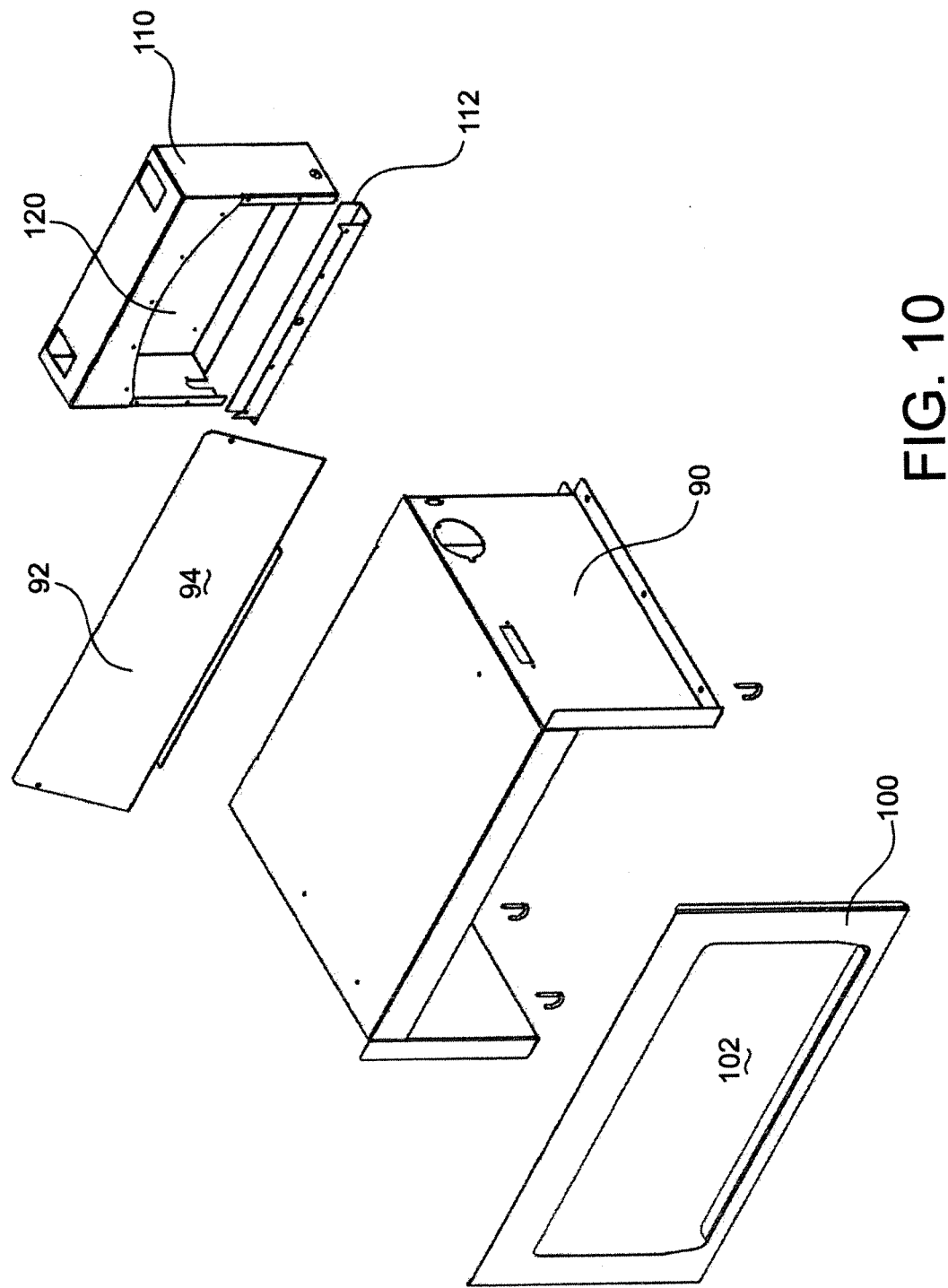
FIG. 10 shows one form of the internal cooking chamber and the portion of the flame chamber in an exploded view.

Heat is provided to the cooking chamber by the first heating system 26, which comprises the chamber heating element 78 and the base heating element 80 as best shown in FIG. 4. The chamber heating element 78 is positioned in the upper region 72 of the cooking chamber 32, and in one form is an electrical type conventional heater. Further, the base heating element 80 can be an electrical type heating member. In one form, the heating element 80 is interposed between the base plate 62 and the lower plate 86. As shown in FIG. 10, an interior casing 90 is provided, which in part defines the cooking chamber. Further shown in this figure is a rear draft plate 92 having a surface 94, which as shown in FIG. 3, helps to define the flame exhaust passage 142. As further shown in FIG. 10, the front plate 100 in part defines the cooking chamber access area 102, which is adjacent to the door 24. Referring now to FIG. 9, a base frame 104 is provided which is configured to house the base heating element 80 and the lower plate 86 thereon.

In general, as shown in FIG. 4, heat is transferred to the cooking chamber 32, not only by the first heating system 26 which comprises the chamber heating element 78 and the base heating element 80, but further heat is transferred from the flame chamber assembly 28 as well.

There will now be a description of the flame chamber assembly 28 with additional reference to FIG. 10, where a flame housing 110 is shown along with the flame trough 112. In general, the flame housing in part comprises the flame chamber 120. The flame chamber 120 as shown in FIG. 3 is positioned behind the transparent member 122. In one form, a backplate 124 is utilized, which as shown in FIG. 5A, has vertical corrugations which are bent, for example, as shown at 126 and concave like vertical vents at 128. The front surface 130 is a reflective surface to reflect the flame, which emits from the flame manifold 132. The flame manifold 132 is adapted to be housed in the flame trough 112, such as that shown in FIG. 10. An igniter 134 ignites combustion gas that is emitted from the upper foraminous surface of the burner element/flame manifold 132. The various orifices of indicated at 136 can be sized to allow a plurality of different gases, such as natural gas, propane or even hydrogen or other combustible material to be passed therethrough. With regard to the burner element 132, the plurality of hole perforations in one form have portions where the hole members are condensed, having a greater number, or the area would have a greater orifice size to create a spiking-like effect along the lateral direction of the burning element 132. As shown in FIG. 5A, the areas for example at 131 have a higher-concentration cluster of open orifices.

Referring now back to FIG. 3, it can be appreciated that an upper surface defining a vent 140 is provided, which is in communication with the flame exhaust 142. The rear draft plate 92 provides the surface 94 as shown in FIG. 10 to allow a venturi-like action as the rising combusted gas passes through the flame exhaust 142, and gas is transmitted through the upper convection vent 150. In general, the lower surface 52 of the inner shell as shown in FIG. 2 and the upper surface 61 of the upper heat containment member 60.

Figure 6:
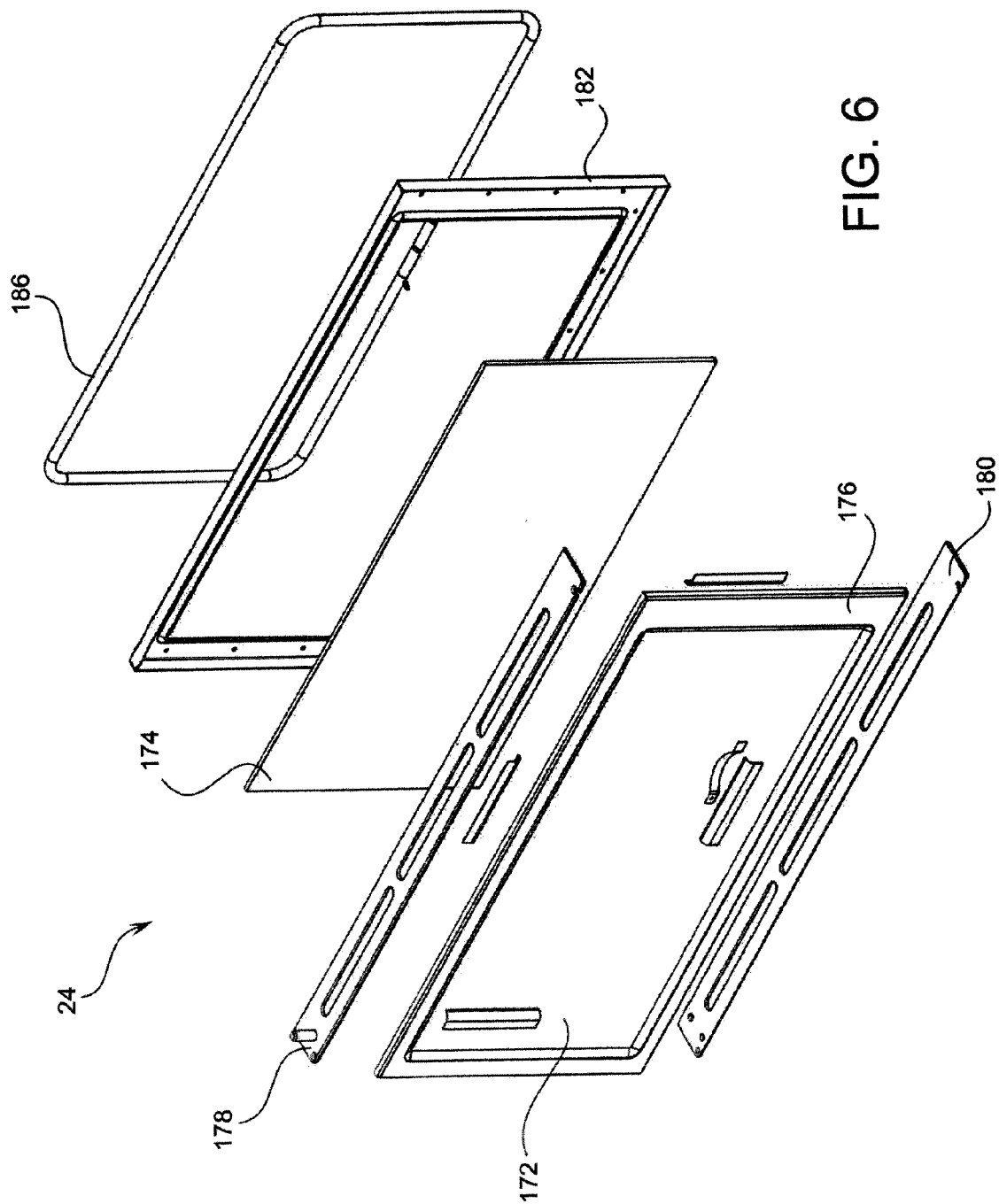
FIG. 6 shows an exploded view of the door.

For further discussion of the upper convection vent 150, there will now be a description of the door 24, with initial reference back to FIG. 1. As shown in the isometric view in FIG. 1, the door is shown in a closed orientation. Referring now to FIG. 6, there is shown an exploded view of the door 24, which in one form comprises an outer transparent member 172 and an inner transparent member 174. The door front panel 176 has upper and lower regions configured to engage the upper bracket 178 and the lower bracket 180. The rear bracket 182 is configured to hold the inner transparent member 174, and in part utilizes a perimeter seal 186.

Figure 7:
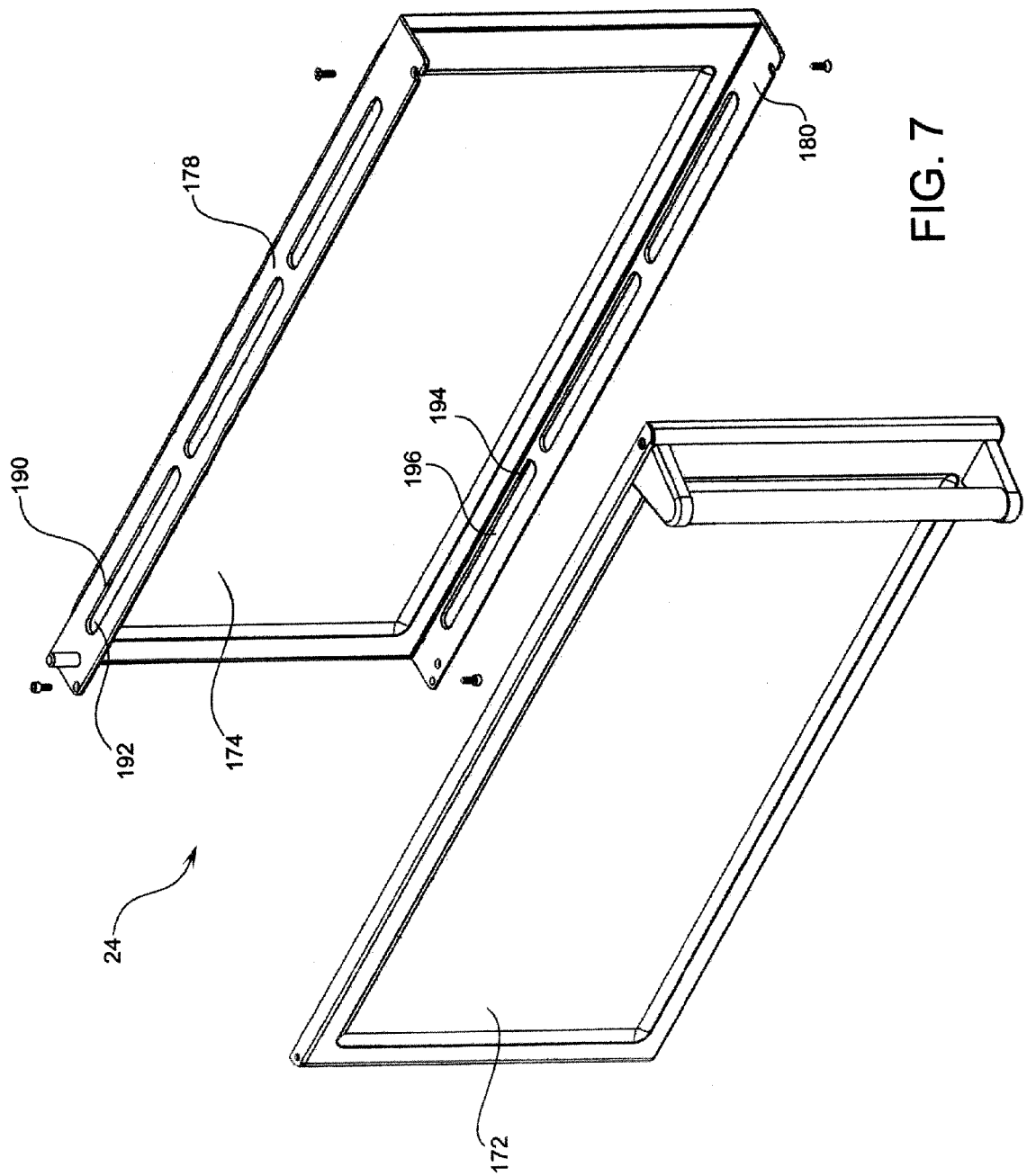
FIG. 7 shows a partially assembled view of the door member.

Referring now back to the upper and lower brackets 178 and 180, as shown in FIG. 7, the upper bracket has a surface 190 defining an opening for the upper vent opening 192. In a similar fashion, the surface 194 defining the opening 196 for the lower vent opening is positioned in the lower portion of the door 24. It should be further noted, with reference to FIGS. 6-8, that the door can be made with two pieces of glass with this cooling effect as illustrated in FIG. 3 by the cooling vector through the upper convection vent 150. It should be noted that many other types of prior art ovens have many pieces of glass to provide a thermal insulation from the outside portion of the oven. However, with the cooling effect, present analysis and experimentation indicates that two pieces of glass can be utilized (in one form) to have a sufficiently cool outer transparent member 172.

Figure 8:
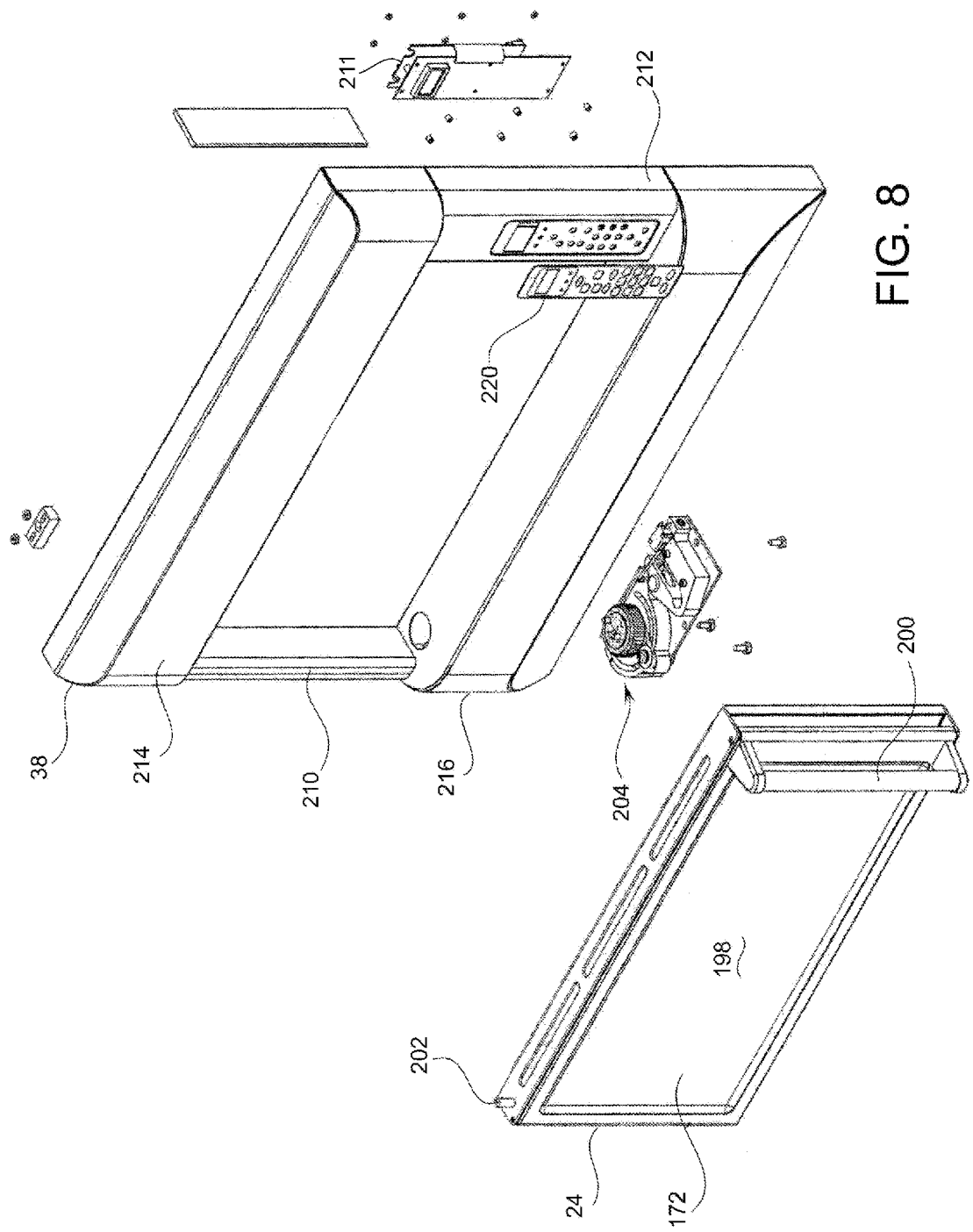
FIG. 8 shows a front panel assembly showing the door member along with the door control mechanism.

The upper and lower vent openings 192 and 196 shown in FIG. 2 allow access to the door chamber 199, which is positioned between the transparent members 172 and 174. Referring now to FIG. 8, it can be appreciated that the outer transparent member 172 and the inner transparent member 174 in part cooperate to make the transparent region 198. As further shown in FIG. 8, a handle 200 can be provided to allow for easy opening of the door, which is pivotally connected at the hinge connection 202. A mechanism 204 is attached to the door and is one form of the door control mechanism 300 as described herein with reference to FIGS. 12-15 and assists in the opening and closing the door and holding it in an open and closed orientation. The front panel 38 as shown in FIG. 8 further comprises the first lateral panel location 210 and the second lateral panel location 212. Further, to aid in the description, there is an upper panel section 214 and a lower panel section 216. Positioned in the second lateral panel section 212 is the interface portion 220 which is described further herein when discussing the control system and power electronics. Still referring to FIG. 8, it should be noted that the front panel section as shown in this figure can have a variety of modular units for a variety of visual effects. FIG. 8 shows one type of a front facade arrangement, but of course other variations can be utilized as well. Further it should be noted that the front door can be removed rather easily from the unit and further separated from the door control mechanism 300 as further described herein.

Now referring back to FIG. 2, with the description of the door 24 in place, there will now be a description of a cooling system utilized in one form of the disclosure. In general, the lower chamber 40 has cooler air positioned therein, and this region is in communication with various openings along the lower panel section 216 of the front panel 38, and these openings are in communication with the lower vent openings 196. Therefore, air from the lower chamber 40 can be directed through the door chamber 199 and out the upper vent openings 192 to the upper convection vent 150.

Therefore, the force of the rising gas through the vent 140 (as shown in FIG. 3) from the combusted gas within the flame chamber 120 tends to have a venturi-like draw of cool air through the upper convection vent 150 and hence through the door chamber 199. This of course allows for cool air to pass through the door chamber to cool the front transparent panel 172.

With regard of the rear draft plate 92, as shown in FIG. 4, an upper lip 93 is provided which increases rigidity given the thermal expansion and causes a buckling effect by making a beam and a greater moment of inertia about its transverse axis. If the angle is too steep or too shallow (too vertical) then the venturi effect may not work effectively to draft the air through the upper convection vent 150 from the door chamber 199. An angle of approximately 20° from vertical +/−15 degrees in the broader scope works effectively to provide a venture like effect.

It should be noted that the transparent panels 172 and 174 do not need to be completely transparent, and the entire panel does not need to be transparent as well. However, a desirable effect of the flame oven 20 is allowing visibility of the flame chamber 120 from the transverse front portion of the flame oven 20. In another form, a flame chamber could, for example, be positioned on the door at the door chamber.

Figure 5B:
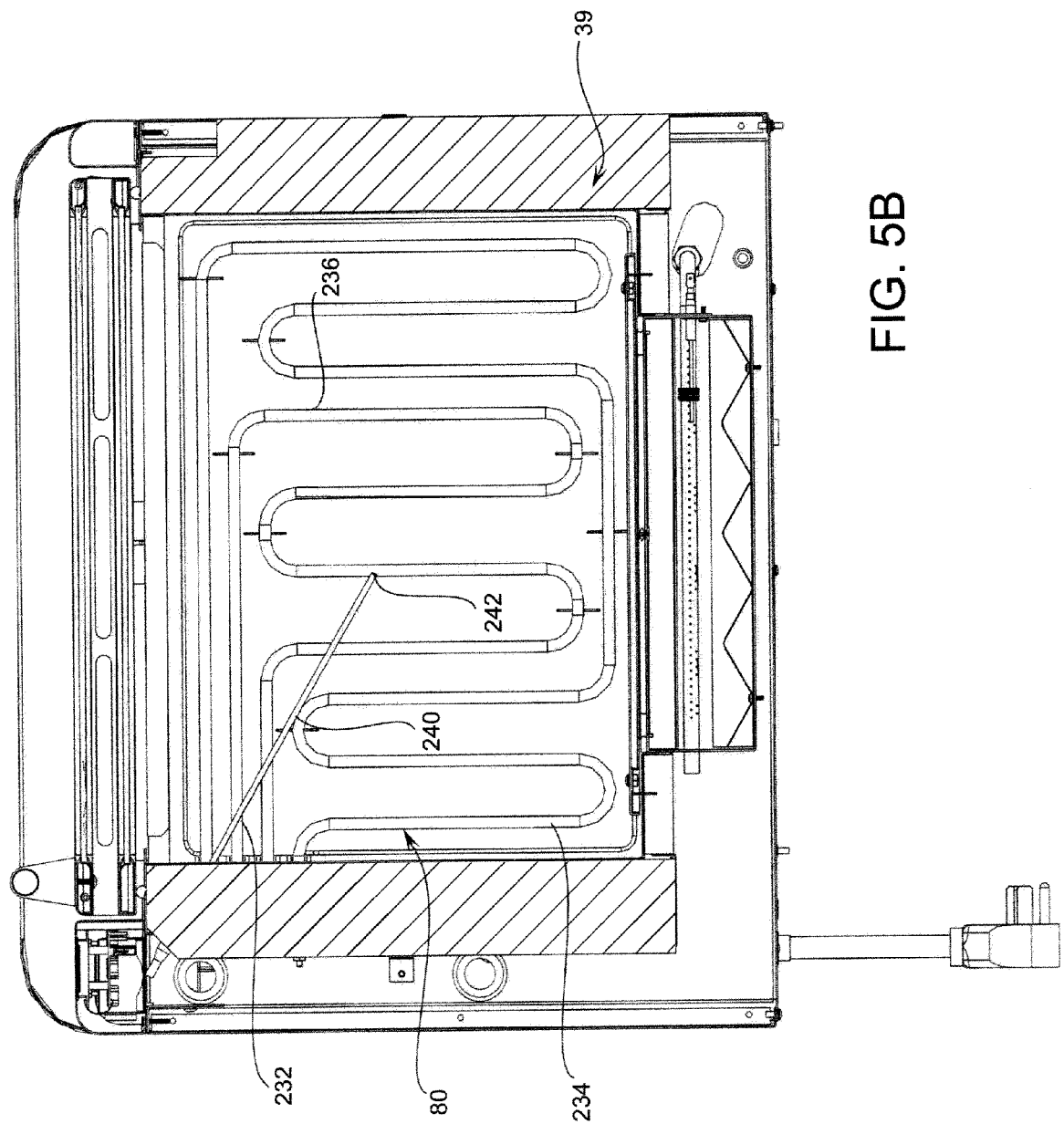
FIG. 5B shows a figure similar to FIG. 5, except the base plate is removed showing the preferred form of a base heating element.

FIG. 5B shows a similar view to FIG. 5A, however the base plate 62 is not shown in this drawing and the base heating element 80 is shown along with the temperature sensor 232, both of which are now described in detail.

As shown in FIG. 5B, the base heating assembly 39 is shown in one form. In general, the base heating assembly comprises the base heating element 80 which in a preferred form is comprised of first and second base heating element members 234 and 236. Each of these heating element members are controlled by the control system discussed further herein. In general, the first and second base heating element members 234 and 236 can have electric current independently directed to either or both members. Of course, one form of having a base heating element 80 is by providing electric resistance heating elements.

Of course, in other forms, the base heating assembly can be provided, including having a disparate network of wires molded directly within the base plate 62 of FIG. 5A, or it could include a induction heating-type system where an inductive magnetic current causes an electronic resistance throughout metallic particles positioned within the base plate 62 and which create heat. Further, a plurality of induction members can be employed to have certain portions heated to accommodate various types of food items taking up different amounts of space on the base plate. As described now herein, the temperature sensor 32 in one form has two temperature sensing locations 240 and 242, as shown in FIG. 5B, which can receive temperature inputs to the control system. The temperature sensor 232 is shown with the extended rod member having first and second temperature sensor/thermocouple elements positioned at the locations indicated at 240 and 242. It can be appreciated that the temperature sensor locations 240 and 242 are positioned near the first and second base heating element members 234 and 236 respectively.

It should be further noted that instead of a an electrical heating element type of oven, the central chamber could be a microwave oven, an induction heating oven, a convection oven, or even a rotisserie type of oven with a flame chamber portion positioned therein.

With reference to FIG. 5B, in one form as previously described, the temperature sensor in the base plate has two locations 240 and 242 to take the temperature in conjunction with the first and second base heating elements 234 and 236. However, additional heating elements can be employed, and the control system can provide different heating temperatures for different zones. For example, looking at the top view of FIGS. 5A and 5B, there could be for example four or more zones of four discrete heaters with four or more temperature sensors corresponding to each region to provide different base heat at different regions for certain applications. One advantage of having several different zones is that in a commercial setting, or a setting where there are different demands upon the oven, one portion of the base heater can be heated to a first temperature, and the other portions can have no heat directed thereto to save energy. Furthermore, different types of menu items that require different base heat temperatures. It should also be noted that in other forms, conventional racks can be positioned within the cooking chamber 32 to provide additional surface area for cooking items therein. Of course in the broader scope the base plate is not a heating element but more of a conventional type of heating system is employed. It should further be noted that the base heating element could be a gas (as opposed to electric) heating element where the chamber, in which the electric element 80 is contained, could be a type of lower combustion chamber to have gas combusted therein providing heat and venting out the rear portion in a similar manner as the flame chamber.

Figure 11:
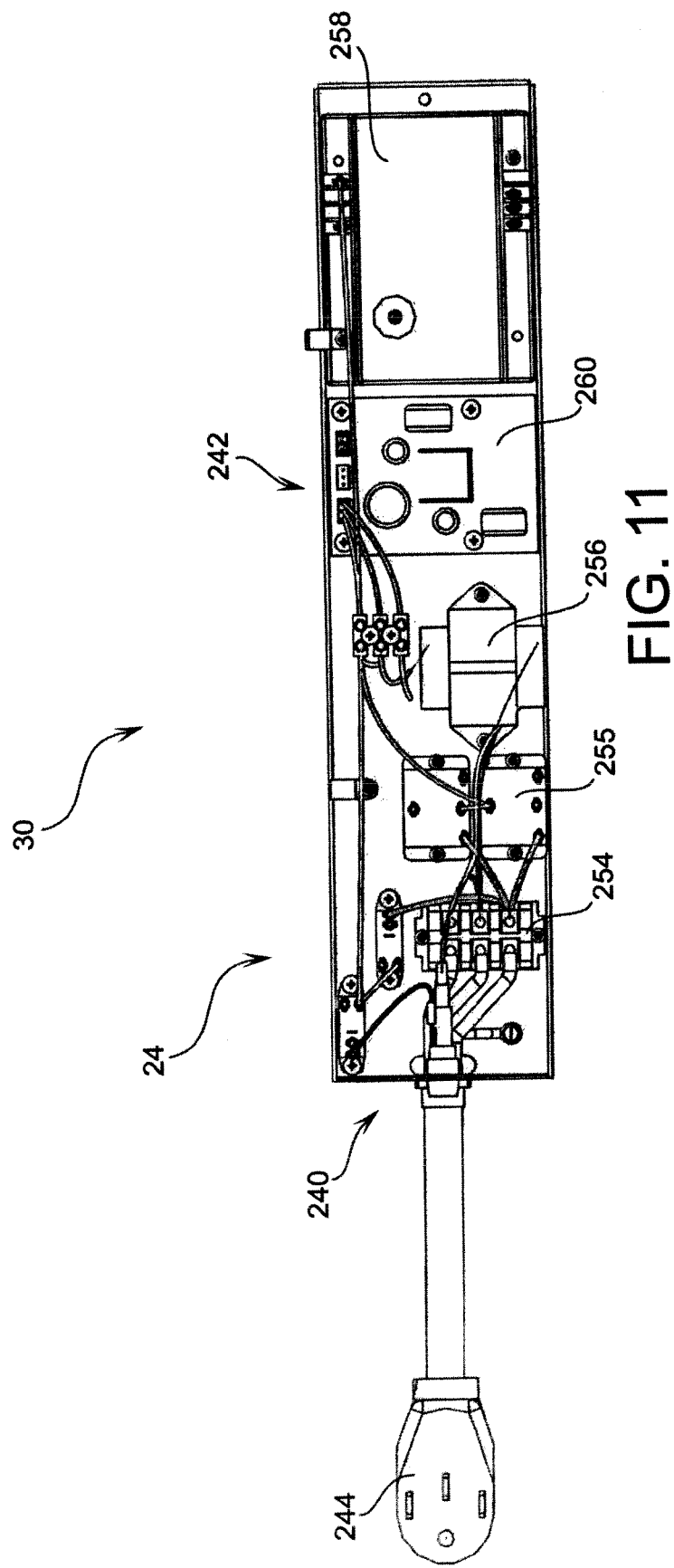
FIG. 11 shows one form of the electronics.
Figure 12:
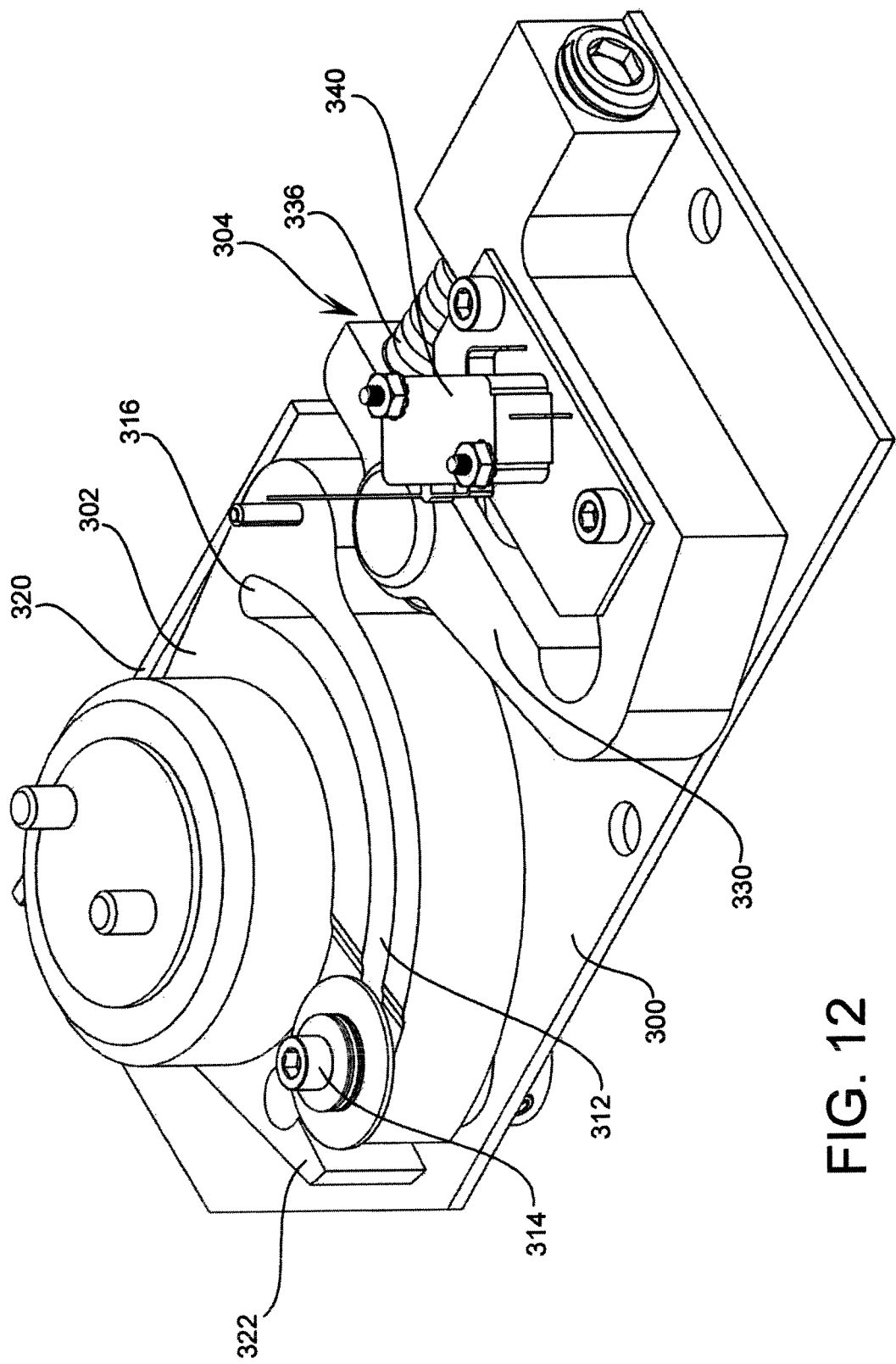
FIG. 12 shows an isometric view of the door control mechanism.

The electronic section 30, which is referred to as the power electronics section 30 is shown in FIG. 11. In general, the power electronics include a power input section 240 and a control system 242. The input from the cord 244 can be either 110, 208, or 220 voltage with a minor modification to the electronics. The control circuit itself in one form is contained within the display module which is shown in FIG. 8 at 211. In one form, a microprocessor controller, which is conventional in the art, is utilized to use the logic.

The cord member 244 in one example transfers electric current to the terminal block 254 where there is a connection and a power feed to the four relays 255 where there is a relay for heaters and one relay for the light. Further power is directed to the transformer 256, and then to the transformer 260 to a 5/12-volt power supply in one form In general, the function of this is to feed power to the relays of 24-volt coils which are desirable because they are easier to handle. A control system is of 5V DC to control various logics which is conventional in the art. Further shown is an ignition module 258 for ignition of the unit.

The control system of the flame oven 20 is configured to control the temperature within the cooking chamber 32. In general as shown in FIG. 5B, the base plate temperature sensor 232 is provided to detect the temperature within the base plate 62. Further, a chamber temperature sensor 230 as shown in FIG. 4 detects the cooking temperature within the cooking chamber 32. The control system, which is a portion of the power electronics 30, in one form where the control system reads temperatures from the temperature sensors to make heat input adjustments. The heating system is independent from the lower portion on the upper chamber. The lower portion has a thermocouple where there is a set point which can be described by the chef or some kind of program. For example the set point is 500° all of the thermocouples attempt to get at 500° and control their respective heaters in that zone. Further, there is desired range for operating, for invoking turning or turning off the relays. For example, this range could be plus or minus 5° in one form. The deadband cannot be too tight of an interval so the relays turn on and off too quickly, or it cannot be too large where the thermal inertia of the unit is so much that the temperatures pick up and exceed this deadband. Therefore, it can be appreciated that the control systems for the lower base heater and the upper convection heater are independent from one another.

There will now be a description of one form of a door control mechanism 300 as shown in FIGS. 12-15. In general, the door control mechanism 300 comprises a rotary member 302 and a base unit 304 which in one form are attached to a base plate 301. Of course the base plate can be any type of structure which is configured to hold the rotary member 302 and the base unit 304 at predefined locations with respect to one another.

Figure 13:
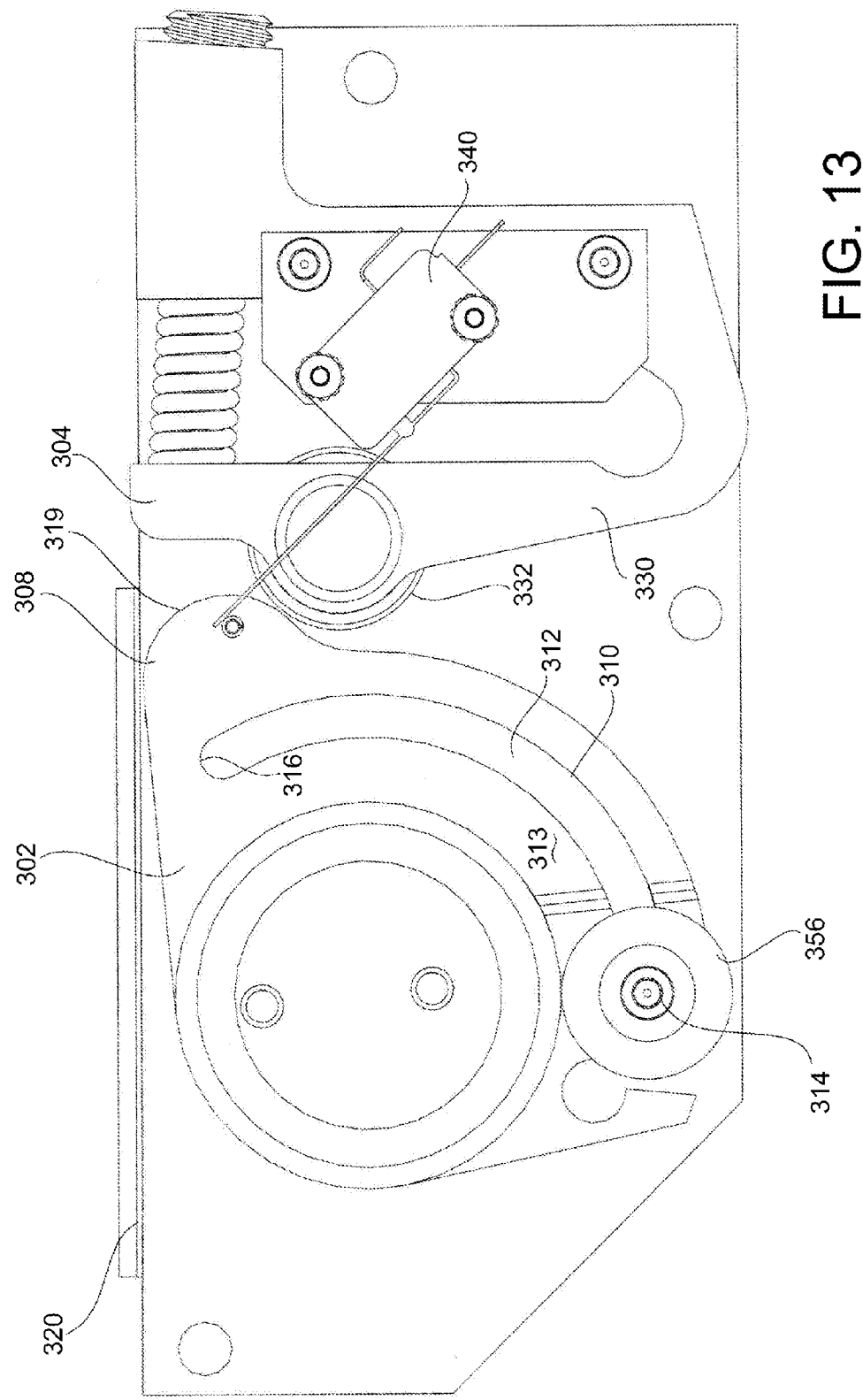
FIG. 13 shows the control mechanism with the rotary member in a closed orientation.
Figure 14:
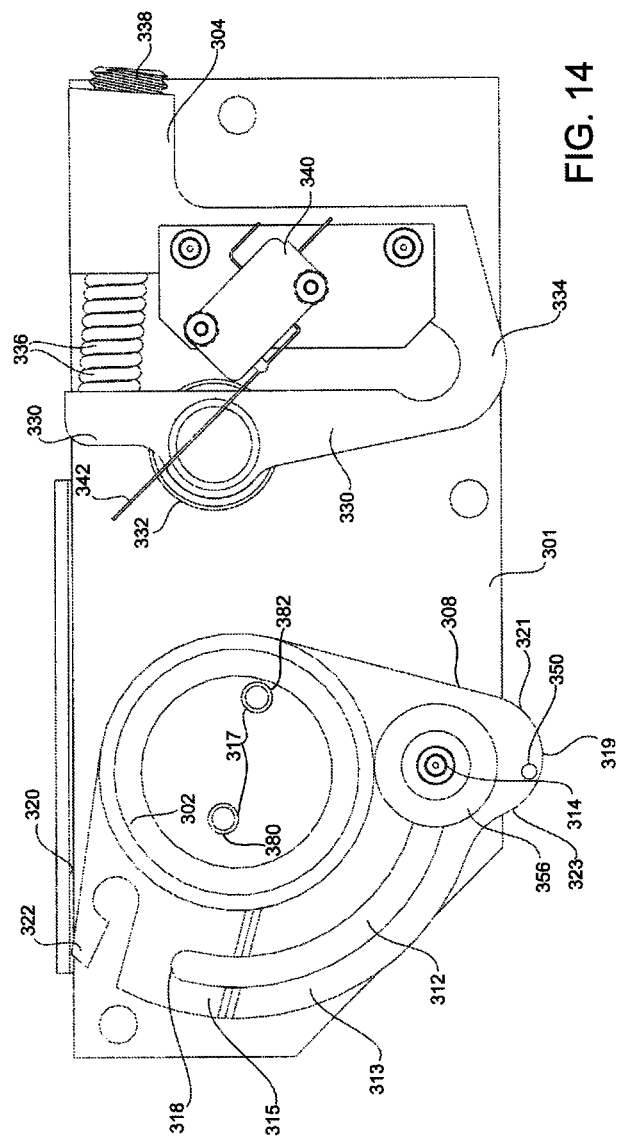
FIG. 14 shows a door control mechanism in the top view where the rotary mechanism is in an open orientation.

The rotary member has a cam extension 308 which is configured to engage the cam engagement/extension portion of the spring member 330 described further herein. In one form, the rotary member has a surface 310 defining an arcuate path 312 where a pin which operates as a travel limiting future 314 is positioned to travel within the arcuate path 312. Referring to FIGS. 13 and 14, the arcuate path 312 has an open stop surface 316 and a close stop surface 318. The surfaces help to find the extreme range of travel of the rotary member 302; however, the stop surface 320 further provides such limitation of rotation. The stop surface 320 is configured to engage the door opened spring stop 322. In one form, the door opened spring stop 322 is a cantilevered spring which as shown in FIG. 14 is configured to engage the surface 320 in order to provide a dampening-like cushioning effect when the door member is swung open. Oftentimes the door has sufficient mass to carry a certain degree of momentum, which can be damaging to the hinges when the door rapidly de-accelerates. Therefore, having a de-acceleration component, such as the door opened spring stop, helps to prevent the door from slamming open.

Referring in FIG. 14, there is shown the base unit 304, which in one form is attached to the base plate 301. The spring member 330 comprises the cam engagement portion 332 which in one form is a reel-like member pivotally attached to the arm portion of the spring member 330. In one form, the spring member 330 is a partial cantilevered spring where the cantilevered portion 334 is positioned at one region, and a secondary spring element 336 is positioned at an opposing region of the cantilevered portion of the spring member. In one form, the secondary spring element 336 is adjustable by way of a thread adjustment screw 338. The threaded adjustment screw can adjust the pre-tension within the spring as well as bias the cam engagement portion 332 toward the rotary member 302. Of course, the threaded adjustment screw 338 is one form of adjusting the secondary spring element 336.

A door closed sensor 340 is provided which can be implemented in a variety of forms. In one form, the extension 342 is positioned toward the rotary member 302 and configured to engage the sensor engaging surface 350 which in one form is a pin-like member.

Figure 15:
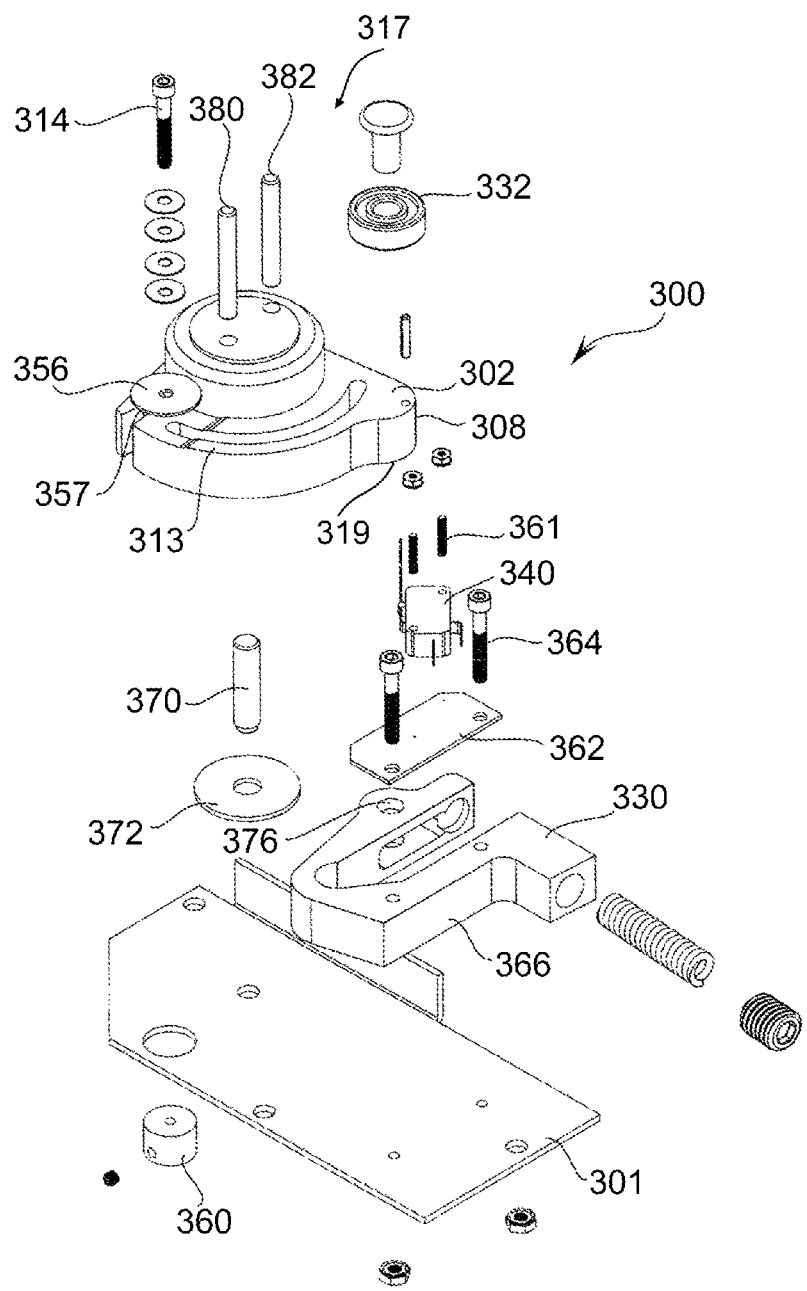
FIG. 15 shows an exploded view of the door control mechanism.

Referring now back to the rotary member 302, it can be appreciated that the cam extension 308 is configured to engage the cam engagement portion 332 of the spring member 330. In one form, the travel limiting feature 314 has a perimeter region 356 having a lower surface which is configured to engage the upper surface 313 of the rotary member 302. The upper surface 313 comprises a detent 315 as shown in FIG. 13, wherein the lower surface of the perimeter region 356 is in less frictional engagement with the upper surface 313 when the rotary member is in the closed orientation. Referring now to FIG. 15, it can be appreciated that the travel limiting feature/pin 314 is shown in an exploded view where the surrounding perimeter region 356 in one form is a washer-like member. The pin 314 (in one form of a travel-limiting future) is attached to the base member 360, and of course can be adjustable to provide a prescribed amount of frictional pre-tension between the lower surface 357 of the perimeter region 356, and the upper surface 313 as shown in FIG. 15. Of course, this is one form of providing a dampening-like mechanism of the range of travel of the door control mechanism. Other forms of a dampening system can also be employed; for example, the frictional force could be placed on the under portion of the rotary member 302 or have a torsion-like dampening system. After the forward surface 321 has disengaged from the cam engagement member, there is no longer an opening or closing force. The frictional force of the surface of the rotary member provides a convenient form of positioning the oven at intermediate locations beyond the engagement of the cam extension 308 and the cam engagement portion 332. In one form, having the door open at least 10° prior to having the cam engagement portion 332 engage the forward surface 321 is a desirable amount of rotation to noticeably indicate to a person watching the oven that the door is clearly open.

Referring to FIG. 15, the exploded view shows one form of carrying out the door control mechanism 300. As shown in this photo, the sensor 340 can be attached by way of fasteners 361 to the plate 362 which in turn is fastened by way of fasteners 364 to the base region 366 of the spring member 330. In one form, the fastener 364 further attaches the spring member 330 to the base plate 301. The pivot pin 370 pivotally attaches the rotary member 302 to the base plate 301. A spacer 372 can be provided to limit the amount of friction therebetween.

The cam engagement portion 332 in one form is a wheel-like member which is pivotally attached at the location 376 on the spring member 330. A wheel-like member is preferred as it will roll around the cam extension 308. The preferred form of connecting the door control mechanism 300 to the actual door is to utilize the first and second pin members 380 and 382 which are offset from the axis of rotation of the rotary member 302 to supply a torque to and from the door to the door control mechanism 300. The attachment point 317 in one form is two pins but of course could be any attachment transferring torque to the door.

Therefore, it can be appreciated that the door control mechanism 300 will operate in a manner such that the cam extension 308 having the outer surface 319 will engage the wheel/cam engagement portion 332 of the spring member 330, and because of the relatively low coefficient of friction therebetween (in one form via a bearing holding the wheel member 332) the door will either be biased to the closed position or clearly biased to an open orientation. As shown in FIG. 14, the surface 319 has a forward surface 321 and a rearward surface 323. Each surface provides a normal force which places a torque upon the rotary member 302. In other words, the door will not be partially closed, but will be open to, for example, at least 20°, which clearly indicates to the door closed sensor 340 whether or not the door is open or closed and further visually indicates to the cook or person responsible for the oven that the door is open. It can therefore be appreciated that the door is forcefully closed, and also forcefully opened after a predefined angle with respect to the oven, and this action occurs without having to have a latch magnet or other type of attachment feature at the portion of the door opposing the hinge region as shown in FIG. 2.

Now referring to FIG. 16, there is shown in a partial sectional view a flame chamber 400 as a standalone unit. In this form, the internal chamber 402 is defined in part by the rear reflection plate 404 and a front transparent member 406. The flame is dispersed through the flame manifold 408, and the flame ignition system 410 ignites the flame in a conventional manner. The upper exhaust port 412 exits the combusted gas. A number types of conventional controllers fuel providers/regulators, similar to that shown at 414, can be provided. In one form, propane is provided therethrough the regulator 414 to the flame chamber 400. In this form, the flame chamber unit can be positioned on the wall or various other places to provide a flame for aesthetic purposes as well as providing a certain amount of heat to the surrounding environment.

It should be noted that in one form there are three different types of phases or states that the oven can be in. One is where the flame acts as a heating element and the oven is functioning as an oven, the flame element is turned off but the secondary heaters (which in one form is in the chamber) and the base plate are activated to heat the food items. Or, if the flame is turned on, for visual effect and for the possible side effect of cooling the entire unit which can be a part of the control system, and the oven secondary heaters are turned off and not in operation. In the latter state the unit 20 is utilized more for aesthetic purposes. Shown herein is one form of carrying out the preferred embodiment where a stand-alone unit is shown. Of course other forms, such as a built-in unit, cabinet or other type of fixtures setting can be employed.

While the present invention is illustrated by description of several embodiments and while the illustrative embodiments are described in detail, it is not the intention of the applicants to restrict or in any way limit the scope of the appended claims to such detail. Additional advantages and modifications within the scope of the appended claims will readily appear to those sufficed in the art. The invention in its broader aspects is therefore not limited to the specific details, representative apparatus and methods, and illustrative examples shown and described. Accordingly, departures may be made from such details without departing from the spirit or scope of applicants' general concept.

We claim:

1. A door control mechanism configured to attach to a door, the door control mechanism comprising:
    a) a base plate,
    b) a rotary member having a door attachment region to attach to the door, a travel limiting surface, and a cam extension,
    c) a base unit and a cantilever spring member, the cantilever spring member positioned to engage the cam extension at a cam engagement portion at an orientation when the rotary member is in a closed orientation with respect to the base unit,
    d) whereas the cam extension is configured to reposition the cantilever spring member to a higher stored energy orientation when the door attached to the rotary member is in a partially closed orientation and the cantilever spring member is configured to release some stored energy to bias the door to a fully closed orientation, and
    e) a travel limiting feature attached to the base and frictionally engaging, and hindering movement of, the travel limiting surface of the cam member from the partially closed orientation to a door fully open position, where the travel limiting surface comprises a detent area where the travel limiting feature does not substantially effect movement of the door from the partially closed orientation to a fully open orientation.

2. The door control mechanism as recited in claim 1 where a door closed sensor is attached to the base plate and is operatively configured to detect when the rotary member is in a closed orientation.

3. The door control mechanism as recited in claim 1 where the spring member has a secondary spring element that is positioned at an opposing region of a cantilevered portion of the spring member.

4. The door control mechanism as recited in claim 3 where the secondary spring element is adjustable to provide various spring force and position of the cam engagement portion into closer engagement toward the rotary member.

5. The door control mechanism as recited in claim 1 where the rotary member has a surface defining an arcuate path where a travel limiting pin is attached to the base plate and configured to travel along the arcuate path to limit the range of motion of the rotary member.

6. The door control mechanism as recited in claim 5 where the surface defining the arcuate path has an open stop surface and a closed stop surface.

7. The door control mechanism as recited in claim 6 where a door opened spring stop is attached to the rotary member and configured to engage a stop surface attached to the base plate where the door opened spring stop engages the stop surface when the door is in an extreme open orientation.

8. The door control mechanism as recited in claim 7 where the door opened spring stop is a cantilevered spring member.

9. A door control mechanism for an oven door that is pivotally attached to an oven having an interior cooking chamber, the door control mechanism comprising:
   a) a rotary member, having an attachment point that is configured to attach to the oven door,
   b) the rotary member having a cam surface and a forward and a rearward sloping portion,
   c) the rotary member further having a travel limiting surface,
   d) a base unit having a cam engagement member,
   e) the cam engagement portion configured to engage the cam surface of the rotary member when the rotary member is in a closed orientation and the door is closed with respect to the oven where the cam engagement member is engaging the rearward surface of the rotary member, and when the door is repositioned toward an open orientation, the cam engagement member transfers from engaging the rearward surface past a high center point to a forward surface to bias the door toward the open orientation
   f) a travel limiting feature attached to the base plate and frictionally engaging, and hindering movement of, the travel limiting surface of the rotary member from the partially closed orientation to a door fully open position, where the travel limiting surface comprises a detent area where the travel limiting feature does not substantially effect movement of the door from the partially closed orientation to a fully open orientation.

10. The door control mechanism as recited in claim 9 where the cam engagement member comprises a spring member which repositions as the door moves between a closed orientation and an open orientation.

11. The door control mechanism as recited in claim 9 where the cam engagement member is a bearing member configured to rotate.

12. A door control mechanism configured to attach to a door, the door control mechanism comprising:
   a) a base plate,
   b) a rotary member having a door attachment region to attach to the door and having a cam extension,
   c) a base unit and a spring member, the spring member positioned to engage the cam extension at a cam engagement portion at an orientation when the rotary member is in a closed orientation with respect to the base unit,
   d) whereas the cam extension is configured to reposition the spring member to a higher stored energy orientation when the door attached to the rotary member is in a partially closed orientation and the spring member is configured to release some stored energy to bias the door fully closed,
   e) where the spring member is a cantilevered spring,
   f) where the spring member has a secondary spring element that is positioned at an opposing region of a cantilevered portion of the spring member,
   g) where the secondary spring element is adjustable to provide various spring force and position of the cam engagement portion into closer engagement toward the rotary member
   h) where the door control mechanism is attached to a flame chambered oven comprising:
   i) a housing having a front region and defining in part a cooking chamber having a forward and rearward transverse region and first and second lateral regions,
   j) a flame chamber having a flame manifold and a transparent member positioned net the rearward transverse region of the cooking chamber, the flame chamber having an upper exhaust vent configured to vent combusted gas therethrough,
   k) a chamber heating system in thermal communication with the cooking chamber and operatively configured to dispense heat thereto,
   l) a door having an interior surface defining a portion of the cooking chamber, the door further having a surface defining an interior chamber,
   m) the housing further having an upper surface defining an upper convection vent in communication with the interior chamber of the door such that combusted gas passing to the upper exhaust vent of the flame chamber is configured to draw gas through the upper convection vent of the housing and further draw gas through the interior chamber of the door and the door control mechanism biases the door to a closed orientation where so the interior chamber of the door is in communication with the upper convection vent of the housing.

13. The flame chambered oven as recited in claim 12 where the interior chamber of the door is defined in part by an outer transparent member and an inner transparent member which are arranged to provide visual access.

* * * * *